US008021694B2

(12) United States Patent
Morelli et al.

(10) Patent No.: US 8,021,694 B2
(45) Date of Patent: *Sep. 20, 2011

(54) ACIDIFIED CHLORITE DISINFECTANT COMPOSITIONS WITH OLEFIN STABILIZERS

(75) Inventors: Joseph P. Morelli, Bothell, WA (US); Karla LaPorte, Redmond, WA (US); Junzhong Li, Apple Valley, MN (US)

(73) Assignee: Ecolab USA Inc., St. Paul, MN (US)

( * ) Notice: Subject to any disclaimer, the term of this patent is extended or adjusted under 35 U.S.C. 154(b) by 832 days.

This patent is subject to a terminal disclaimer.

(21) Appl. No.: 11/106,798

(22) Filed: Apr. 15, 2005

(65) Prior Publication Data

US 2005/0184273 A1    Aug. 25, 2005

Related U.S. Application Data

(63) Continuation-in-part of application No. 10/374,690, filed on Feb. 25, 2003, now Pat. No. 6,916,493, which is a continuation of application No. 09/859,902, filed on May 16, 2001, now Pat. No. 6,524,624.

(51) Int. Cl.
*A61K 33/14* (2006.01)
*A61K 8/00* (2006.01)
*A01N 37/00* (2006.01)
*A01N 25/34* (2006.01)
*A01N 25/00* (2006.01)

(52) U.S. Cl. .......... 424/661; 424/53; 424/404; 424/405; 514/553

(58) Field of Classification Search ................. 424/661, 424/53, 404, 405; 514/553
See application file for complete search history.

(56) References Cited

U.S. PATENT DOCUMENTS

| 2,061,617 | A | | 11/1936 | Downing et al. |
| 2,572,605 | A | | 10/1951 | Fincke |
| 3,444,191 | A | | 5/1969 | Nielsen |
| 3,845,114 | A | | 10/1974 | Sweeney et al. |
| 4,330,531 | A | | 5/1982 | Alliger |
| 4,585,482 | A | | 4/1986 | Tice et al. |
| 4,861,514 | A | | 8/1989 | Hutchings |
| 4,963,287 | A | | 10/1990 | Hutchings et al. |
| 5,068,418 | A | * | 11/1991 | Kulprathipanja et al. .... 562/580 |
| 5,185,161 | A | | 2/1993 | Davidson et al. |
| 5,252,343 | A | | 10/1993 | Kross |
| 5,820,822 | A | | 10/1998 | Kross |
| 6,020,293 | A | * | 2/2000 | Ahmed et al. ................. 510/193 |
| 6,043,391 | A | | 3/2000 | Berger et al. |
| 6,123,966 | A | | 9/2000 | Kross |
| 6,379,685 | B1 | | 4/2002 | Richter et al. |
| 6,383,541 | B1 | | 5/2002 | Danner et al. |
| 6,436,444 | B1 | | 8/2002 | Richter et al. |
| 6,524,624 | B1 | | 2/2003 | Morelli et al. |
| 6,599,432 | B2 | | 7/2003 | Kross et al. |
| 6,699,510 | B2 | | 3/2004 | McSherry et al. |
| 2002/0122854 | A1 | | 9/2002 | Danner et al. |
| 2003/0206971 | A1 | | 11/2003 | McSherry et al. |
| 2005/0184273 | A1 | | 8/2005 | Morelli et al. |

FOREIGN PATENT DOCUMENTS

| CH | 575762 | | 5/1976 |
| DE | 2525685 | | 12/1976 |
| EP | 0287074 | | 10/1988 |
| EP | 0565134 | | 10/1993 |
| EP | 0482811 | | 4/1997 |
| EP | 0904693 | | 3/1999 |
| EP | 0906724 | A1 * | 7/1999 |
| WO | WO99/16309 | | 4/1999 |
| WO | WO99/16418 | | 4/1999 |
| WO | WO00/01423 | | 1/2000 |
| WO | WO02091832 | | 11/2002 |
| WO | WO2004/004677 | | 1/2004 |
| WO | WO2004/032979 | | 4/2004 |

OTHER PUBLICATIONS

Chemical Abstracts 105: 29821, abstracting JP 61-20557, 1986, 1 page.
InterSept & BiSept: The Guide Book, Westfailia Surge Inc. Jun. 1, 2004, 3 pages.
McCutcheon's Emulsifiers & Detergents, The Manufacturing Confectioner publishing Co., Glen Rock, NJ, vol. 1, North American Edition, 1996, p. 31, entry for "Bio-Terge AS-40", 2 pages.
PROMT Abstract, accession No. 83:100151 (1983), 1 page.
WPIDS (Derwent) abstract, accession No. 1986-301647, abstracting JP 61-223082, 1986, 1 page.

* cited by examiner

*Primary Examiner* — Johann Richter
*Assistant Examiner* — Abigail Fisher
(74) *Attorney, Agent, or Firm* — Andrew D. Sorensen; Laura C. DiLorenzo

(57) ABSTRACT

A two-part disinfecting systems, as well as disinfecting compositions and methods for making and using the same. The two-part disinfecting system contains a first part and a second part adapted to be mixed to yield an aqueous disinfecting composition, wherein the first part comprises a chlorite and the second part comprises an acid, and wherein the first part, the second part, or both the first and second parts comprise an olefin compound.

16 Claims, No Drawings

ACIDIFIED CHLORITE DISINFECTANT COMPOSITIONS WITH OLEFIN STABILIZERS

CROSS REFERENCE TO RELATED APPLICATION

This application is a continuation-in-part of U.S. patent application Ser. No. 10/374,690, filed Feb. 25, 2003, now U.S. Pat. No. 6,916,493 which is a continuation of U.S. patent application Ser. No. 09/859,902, filed May 16, 2001, now U.S. Pat. No. 6,524,624, both of which are incorporated herein by reference in their entirety.

FIELD OF THE INVENTION

The present invention relates to two-part disinfecting systems, as well as disinfecting compositions and methods for making and using the same, and in a particular embodiment to a two-part disinfecting system that, when mixed, yields a disinfecting composition having reduced chlorine dioxide generation and extended color longevity.

BACKGROUND OF THE INVENTION

Many diseases arise from the growth and spread of microorganisms that can affect all aspects of life, from human health, to animal health, to food and water safety, to the safety of the environments we live in. Disinfectants have found wide spread application in all these areas. Hospitals perform rigorous programs to disinfect and sterilize their environments. Consumer homes are replete with disinfectant hand cleaners, sprays, hard surface cleaners, disinfectant wipes, and fruit and vegetable washes. Disinfectants are widely used on farms where the difference between healthy and sick animals can mean the difference between profitability and loss.

Mastitis is one of the most common and economically costly diseases confronting milk producers. Economic losses result from poorer milk quality, lower milk production, and potential culling of chronically infected animals. The use of disinfectant solutions both before and after milking has found great success in preventing mastitis, particularly disinfectants based on acidified chlorite such as those commercially available from Alcide Corporation (Redmond, Wash.) and Ecolab Inc. (St. Paul, Minn.), and disclosed in U.S. Pat. Nos. 6,524, 624, and 6,699,510.

Acidified chlorite (AC) disinfectants are commonly used as two-part products having a first part containing a chlorite (such as sodium chlorite) and a second part containing an acid. The AC disinfectant is formed upon mixing the first and second parts, and typically only in amounts sufficient for a given use period. Depending upon the desired characteristics and/or intended use of the AC disinfectant, either the first or second part, or both parts, may contain one or more optional ingredients such as skin conditioners, healing agents, surfactants, thickeners, builders, film-forming agents, and/or preservatives. Also, depending upon the two-part system, the AC disinfecting composition may be formed by simply mixing the first and second parts, often in approximately equal volumes, or may involve some additional dilution step before or after mixing.

Color has proved to be an important attribute for teat disinfectants, allowing farmers to visually confirm that the disinfectant has been properly applied to the teat. This is particularly advantageous for confirming application to large herds when multiple farm workers are applying the disinfectant to many different animals. Unfortunately, many such colorants used to impart the color are subject to chemical degradation upon formation of the AC disinfectant. Once the chlorite-containing part and acid part are combined, they form chlorous acid. Over time, the chlorous acid undergoes complex chemical transformations to form chlorine dioxide. Formation of too much chlorine dioxide is undesirable because chlorine dioxide is a gas in its natural state, which is noxious; chlorine dioxide can be corrosive to metal surfaces; and chlorine dioxide degrades colorants. Colorant degradation leads to ineffective coloration and teat marking as the disinfectant ages—that is, from the point in time following mixing of the first and second parts to form the AC disinfectant.

Teat disinfectants are generally considered animal "drugs" in most countries, and thus controlled by the regulatory agencies overseeing the same. Most often, the only colorants that can be used in a teat disinfectant are those dyes that have been approved for use in food and/or drugs. For example, in the United States approved dyes can be found in 21 C.F.R. §70.3. When present in an AC disinfectant, these dyes are susceptible to chemical oxidation and rapidly lose their color following formation of the disinfectant.

Previous attempts to address this problem have largely focused on use of pigments as opposed to dyes (see e.g., WO 99/16418, WO 99/16309 and EP 0 904 693 A1). Pigments are insoluble colorants and less susceptible to chemical degradation within the AC disinfectant. However, pigments are plagued by problems associated with settling out of solution, staining parlor floors, and clogging milk filters. In addition, such pigments are not approved in some countries for use in teat disinfectants since they are not approved for food or drug use by their regulatory agencies.

Accordingly, there remains a need in the art for improved AC disinfectants generally, as well as a need for controlling the formation of chlorine dioxide and consequently improving the color longevity of dyes within AC disinfectants, particularly those dyes that have been approved for use in food and drugs. The present invention fulfills these needs and provides further related advantages.

SUMMARY OF THE INVENTION

In one embodiment, the present invention provides a two-part disinfecting system comprising a first part and a second part adapted to be combined to yield an aqueous disinfecting composition. The first part comprises a chlorite and the second part comprises an acid. In addition, the first part, the second part, or both the first and second parts further comprise an olefin compound having the formula:

$(R_1)CH=CH(R_2)(X)$ where $R_1 =H-$, $CH_3^-$, $CH_3(CH_2)_n-$, $CH_3(CH_2)_n CH(OH)-$, and

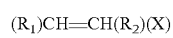
$MO_2C(CH_2)_n-$;

n=1-20 and preferably 1-10;

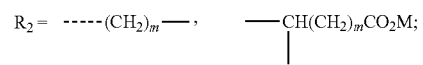
$R_2 = -----(CH_2)_m-$,   $-CH(CH_2)_m CO_2 M$;

m=2-20 and preferably 2-10;
M=H, Na, K, Ca, Mg, ammonia, or an organic cation such as monoethanolamine, or triethanolamine; and X=a hydrophilic group having at least four heteroatoms selected from the group consisting of oxygen, nitrogen, sulfur, chlorine, bromine, fluorine, iodine, phosphorous and mixtures thereof, wherein there are at least two saturated carbon atoms between $(R_1)CH=CH$ and a heteroatom and a saturated carbon is a carbon free of double and triple bonds.

The olefin compound may be in a protonated form (i.e., sulfonic acid), a salt form, or a mixture thereof, and generally contains from 6 to 60 carbon atoms, although it is understood that more or fewer carbons would fit within the invention.

Alpha olefin sulfonates have been previously discussed as compositions that aid in reducing the generation of chlorine dioxide. See U.S. Pat. No. 6,524,624 and U.S. patent application Ser. No. 10/374,690.

Now, it has been discovered that a specific olefin chemical structure has been found to be especially effective at reducing chlorine dioxide generation. In particular, it has been discovered that an olefin compound having a hydrocarbon chain with at least one double bond that is at least two saturated carbon atoms away from a hydrophilic group having at least four heteroatoms are especially effective.

These olefin compounds are advantageous for three reasons. First, they provide a formulator with a broader range of materials to select from where there are broader choices for foaming, wetting, and cleaning characteristics. Second, some are effective at reducing chlorine dioxide generation and consequently color degradation in smaller quantities than alpha olefin sulfonates. Third, some alpha olefin sulfonates can be drying to skin at elevated levels. Some olefin compounds of the present invention are less drying than the alpha olefin sulfonates.

When combined, the first part and second part form a disinfecting composition having utility over a wide range of applications. The olefin compound has surprisingly been found to reduce the generation of chlorine dioxide, providing a disinfecting composition that is longer lasting, and has less odors. When the optional oxidizable colorant is present, this results in a disinfecting composition having extended color longevity. Such compositions are particularly useful as teat dips, as well as for other disinfecting applications where reduction in the generation of chlorine dioxide or extended color longevity is desirable.

In a further embodiment, a method for making a disinfecting composition is disclosed by combining the first part and the second part of the two-part disinfecting system. Such combination may involve mixing liquid forms of the first part and second part, or may involve diluting or dissolving the first part and/or second part prior to mixing, at the time of mixing, and/or after mixing.

In yet another embodiment, a method for disinfecting a substrate is disclosed by contacting the substrate with an effective amount of a disinfecting composition of this invention. Such substrates include any surface, material, or fluid that would benefit from being disinfected, including the skin or tissue of a warm-blooded animal, in particular the teat of a dairy cow, goat or sheep, as well as hard surfaces generally and food surfaces such as meat and meat parts (including cooked and uncooked beef, poultry, pork, other generally recognized red meats, and fish), fruits and vegetables, and process waters, such as flume waters, cooling tower waters, equipment, and facility cleaning solutions, etc.

These and other aspects of this invention will be evident upon reference to the following detailed description of the invention.

DETAILED DESCRIPTION OF THE INVENTION

Definitions

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

Weight percent, percent by weight, % by weight, wt %, and the like are synonyms that refer to the concentration of a substance as the weight of that substance divided by the weight of the composition and multiplied by 100.

The recitation of numerical ranges by endpoints includes all numbers subsumed within that range (e.g. 1 to 5 includes 1, 1.5, 2, 2.75, 3, 3.80, 4 and 5).

As used in this specification and the appended claims, the singular forms "a," "an," and "the" include plural referents unless the content clearly dictates otherwise. Thus, for example, reference to a composition containing "a compound" includes a mixture of two or more compounds. As used in this specification and the appended claims, the term "or" is generally employed in its sense including "and/or" unless the content clearly dictates otherwise.

The use of the terms "antimicrobial" and "biocide" in this application does not mean that any resulting products are approved for use as an antimicrobial agent or biocide.

As noted above, in one embodiment a two-part disinfecting system is disclosed comprising a first part and a second part adapted to be combined to yield an aqueous disinfecting composition. The first part comprises a chlorite and the second part comprises an acid. In addition, the first part, the second part, or both the first and second parts, further comprise an olefin compound.

Acidified chlorite compositions may be generated by combining chlorite (i.e., $ClO_2^-$), typically in the form of a metal salt such as sodium chlorite, with an acid activator. Such compositions are effective disinfectants due to the generation of antimicrobial oxidants, particularly chlorous acid (i.e., $HClO_2$). Chlorous acid is formed very rapidly upon acidification of chlorite in an equilibrium process governed by the solution pH. Chlorous acid can subsequently undergo a series of chemical reactions to form chlorine dioxide. Although not wishing to be limited by the following theory, it is believed that the olefin compound reduces generation of chlorine dioxide upon formation of the disinfecting composition by affecting the rate by which chlorous acid is converted to chlorine dioxide. When an oxidizable colorant is present, it is degraded in significant part by the chlorine dioxide generated within the disinfectant. Thus, the olefin compound, by controlling chlorine dioxide generation, imparts extended color longevity to the disinfecting composition by limiting oxidation of the colorant. Chlorine dioxide is a particularly pungent gas that can be unpleasant at excessive levels in air. Unlike chlorous acid, which stays in solution at the surface being disinfected, chlorine dioxide can escape into the air around the user. Slowing the rate of chlorine dioxide formation leads to a longer lasting disinfectant composition with less odors to the user.

The first and second parts may both be in the form of an aqueous composition, emulsion, microemulsion, cream or gel, or one or both may be in a concentrated, non-aqueous or solid form. For example, the first and second parts may be aqueous compositions or gels to be mixed in approximately equal volumes to form the disinfecting composition, or may be concentrates or solids to be diluted by or dissolved in water, and then mixed to yield the disinfecting composition. Alternatively, the first and/or second parts may be in a non-aqueous or solid form (such as a powder or tablet) to be mixed with or dissolved in water prior to combination. To avoid excessive generation of chlorine dioxide which may occur upon combination of concentrated forms, it is preferable to mix the first and second parts after the parts are diluted with or dissolved in water.

The chlorite of the first part is typically an alkali or alkaline earth metal chlorite, such as potassium or sodium chlorite, and more typically sodium chlorite. The chlorite is present in the first part in an amount such that, when combined with the second part, it is present within the disinfecting composition at a concentration ranging from about 0.005% to about 3% by weight, from about 0.05% to about 0.5% by weight, and from about 0.1% to about 0.4%.

The acid of the second part is any compound or mixture of compounds that will acidify the chlorite of the first part. In one embodiment, the acid has a $pK_a$ ranging from 2 to 5. The acid can be an organic acid, inorganic acid, or mixture thereof. Organic acids include (but are not limited to) formic acid, acetic acid, glycolic acid, lactic acid, pyruvic acid, malic acid, mandelic acid, citric acid, tartaric acid, adipic acid, succinic acid, malonic acid, propionic acid, heptanoic acid, octanoic acid, nonanoic acid, salicylic acid, benzoic acid, gluconic acid, or mixtures thereof. The organic acid can also be alkyl alkylarl-, and arylsulfonic acids such as octanesulfonic acid, toluenesulfonic acid, cumenesulfonic acid, dodecylbenzenesulfonic acid, and homo- & copolymers containing poly(styrenesulfonic acid) and poly(acrylamidopropylsulfonic acid). Inorganic acids include (but are not limited to) sulfuric acid, sulfamic acid, phosphoric acid, hydrochloric acid, nitric acid, boric acid, or mixtures thereof. Other acids that may be used include (but are not limited to) hydrated metals salts of iron, aluminum, zirconium, vanadium, and gadolinium as described in U.S. Pat. No. 5,820,822. Acids also include (but are not limited to) solid acid exchange resins, such as Amberlite™, Diaion™, Dowex™ and Duolite™, as well as aluminum silicate zeolites. Alternatively, the acid may be any organic acid precursor which forms an acid upon contact with water, such as acid anhydrides, esters, and sulfonate esters. Examples of organic acid precursors are described in U.S. Pat. No. 4,585,482.

The acid is present in the second part in an amount such that, when combined with the first part, it is present within the disinfecting composition at a concentration ranging from about 0.05% to about 10% by weight, from about 0.5% to about 5.0% by weight, and from about 1.0% to about 3.0% by weight.

Alternatively, the amount of acid in the second part may be characterized by the pH of the disinfecting composition. In this regard, the acid is present in the second part in an amount such that, when combined with the first part, the pH of the disinfecting composition is below about 5, from about 2 to about 5, and from about 2.3 to about 3.5.

The optional oxidizable colorant is a colorant that undergoes color loss upon contact with chlorine dioxide at concentrations generally encountered in acidified chlorite disinfectants. The colorant may be present in the first or second part and is preferably present in the second part. Such colorants are typically soluble in vehicles which may be used as carriers for the first or second part, including (but not limited to) water, alcohol, glycerin and/or oil. In the practice of this invention, either a single oxidizable colorant, or a mixture of two or more oxidizable colorants, may be present in the second part. The amount of oxidizable colorant present in the first or second part is an amount that, upon combination with the other part, will impart the desired color and/or color intensity to the disinfecting composition.

In the United States, colorants for use in foods and/or drugs are generally classified by the Food and Drug Administration (FDA) as either (1) a food, drug and cosmetic (FD&C) colorant, (2) a drug and cosmetic (D&C) colorant, or (3) an externally applied drug and cosmetic (Ext. D&C) colorant. These colorants may be identified using Colour Index Numbers (CI#) established by the Society of Dyers and Colourists (UK) and the American Association of Textile Chemists & Colorists (Color Index, Society of Dyers and Colorists and American Association of Textile Chemists & Colorists, Rev. 3.sup.rd ed, Branford, 1975).

Representative FD&C colorants include (but are not limited to) FD&C Blue #1 (CI#42090), FD&C Blue #2 (CI#73015), FD&C Green #3 (CI# 42053), FD&C Red #3, FD&C Red #4 (CI# 14700), FD&C Red #40 (CI# 16035), FD&C Yellow #5 (CI# 19140), FD&C Yellow #6 (CI# 15980), Orange B, and Citrus Red #2.

Representative D&C colorants include (but are not limited to) D&C Violet #2 (CI# 61565), D&C Green #5 (CI# 61570), D&C Green #6 (CI# 61565), D&C Green #8 (CI# 59040), D&C Orange #4 (CI# 15510), D&C Yellow #7, D&C Yellow #8 (CI# 45350), D&C Yellow #10 (CI# 47005), D&C Yellow #11 (CI# 47000), D&C Red #6 (CI# 15850), D&C Red #17 (CI# 26100), D&C Red #22 (CI# 45380), D&C Red #28 (CI# 45410), and D&C Red #33 (CI# 17200).

Representative Ext. D&C colorants include (but are not limited to) Ext. D&C: Violet #2 (CI# 60730), Ext. Yellow #7 (CI# 10316), Other representative food colorants include (but are not limited to) Acid Green 1 (CI# 10020), Food Yellow 2 (CI# 13015), Acid Yellow 36 (CI# 13065), Food Yellow 8 (CI# 14720), Acid Orange 20 (CI# 14600), Food Red 3 (CI# 14720), Food Red 2 (CI# 14815), Acid Red 88 (CI# 15620), Food Orange 2 (CI# 15980), Acid Red 26 (CI# 16150), Food Red 7 (CI# 16155), Food Red 9 (CI# 16135), Acid Orange 10 (CI# 16230), Acid Red 18 (CI# 16255), Acid Red (CI# 16290), Acid Red 1 (CI# 18050), Acid Red 155 (CI# 18130), Acid Yellow 121 (CI# 18690), Acid Red 180 (CI# 18736), Acid Yellow 11 (CI# 18820), Acid Yellow 40 (CI# 18950), Acid Yellow 5 (CI# 18965), Acid Black 1 (CI# 20470), Acid Red 163 (CI# 24790), Acid Red 73 (CI# 27290), Food Black 2 (CI# 27755), Food Black 1 (CI# 28440), Direct Orange 34 (CI# 40215), Acid Blue 3 (CI# 42051), Acid Blue 5 (CI# 42052), Green S (CI# 44090), and Brown HT (CI# 20285).

In addition, oxidizable colorants also include naturally occurring colorants such as red cabbage extract, beet root extract, carminic acid, curcumin, beta carotene, annatto extract, grape skin extract, astaxanthin, canthaxanthin, henna, guaiazulene, and mixtures thereof.

Oxidizable colorants of this invention also include any combination of two or more of the above FD&C, D&C, Ext. D&C, food colorants, and naturally occurring colorants. Furthermore, the oxidizable colorant may, upon contact with the other part, undergo a change in color. Such color change may be attributable, for example, to a change in pH going from the pH of one part to the pH of the resulting composition. Alternatively, either part may optionally contain a colorant such that, when combined with the other part, the resulting composition has a color different from either the first and second parts.

As noted above, it has been surprisingly found that the presence of an olefin compound in either the first part, the second part, or both the first and second parts, reduces the generation of chlorine dioxide in the resulting disinfecting composition. As a result, when the optional oxidizable colorant is present, the olefin compound imparts enhanced color longevity to the disinfection composition. As used herein, an "olefin compound" refers to a hydrocarbon having at least one double bond that is at least two saturated carbon atoms away from a hydrophilic group having at least four heteroatoms selected from the group consisting of oxygen, nitrogen, sulfur, chlorine, bromine, fluorine, iodine, phosphorous and mixtures thereof. The term "hydrophilic" refers to the portion of the molecule that tends to be "water-loving" or more soluble. The term "saturated carbon" refers to a carbon atom that is free of double or triple bonds. The olefin compound of the present invention has the following structure:

$(R_1)CH = CH(R_2)(X)$ where $R_1 =$ H—, $CH_3$—, $CH_3(CH_2)_n$—, $CH_3(CH_2)_n CH(OH)$—, and $MO_2C(CH_2)_n$—;

n=1-20 and preferably 1-10;

$R_2 =$ , —CH(CH$_2$)$_m$CO$_2$M;

m=2-20 and preferably 2-10;
M=H, Na, K, Ca, Mg, ammonia, or an organic cation such as monoethanolamine, or triethanolamine; and
X=a head group having at least four heteroatoms selected from the group consisting of oxygen, nitrogen, sulfur, chlorine, bromine, fluorine, iodine, and phosphorous and mixtures thereof, wherein there are at least two saturated carbon atoms between $(R_1)CH$=CH and a heteroatom and a saturated carbon is a carbon free of double and triple bonds.

Because of the presence of the hydrophobic group $(R_1)CH$=CH$(R_2)$ and the hydrophilic group (X), the olefin compounds of the present invention exhibit surfactant properties, and consequently can be characterized in terms of their HLB (Hydrophile-Lipophile Balance) value. The HLB is an expression of the relationship between the hydrophobic group and the hydrophilic group of the molecule. Generally, the higher the HLB value, the more water-soluble the molecule. Hydrophilicity increases with increasing number of heteroatoms. HLB values greater than 10 are considered water-soluble. For the present invention, the olefin compound preferably has a HLB value equal to or greater than 8, and more preferably equal to or greater than 12.

Some non-limiting examples of suitable olefin compounds include those compositions that are oleyl-based, ricinoleyl-based, and undecylenyl-based. Oleyl based compounds are compounds derived from oleic acid. This includes addition products in the form of esters, amides, oxazolines, and ene synthesis (hydro-allyl-addition) adducts. It also includes derivatives formed by converting oleic acid into oleyl alcohol or oleyl amine and further chemically modifying the alcohol and amine groups. Ricinoleyl- and undecylenyl-based compounds refer to the analogous array of compounds derived from the corresponding ricinoleic acid and undecylenic acid, respectively.

Some non-limiting examples of oleyl-based olefin compounds include those having the following structure:

$CH_3(CH_2)_7 CH = CH(CH_2)_7$—X

Examples of substructures that may be used as the —X group are provided in Table 1.

TABLE 1

| Oleyl-Based-X Groups | | |
|---|---|---|
| Substructure-X | INCI Name | Example Trade Names |
| (CO)NCH$_3$CH$_2$CH$_2$SO$_3$Na | Sodium Methyl Oleoyl Taurate | Geropon T-77 (Rhodia) Hostapon T (Hoechst Celanese) |
| (CO)N(CH$_2$CH$_2$OH)$_2$ | Oleamide DEA | Incromide OD (Croda) Mackamide NOA (McIntyre) |
| (CO)NH(CH$_2$)$_3$N(CH$_3$)$_2$→O | Oleamidopropylamine oxide | Incromine Oxide O (Croda) Mackamine OAO (McIntyre) |
| (CO)NH(CH$_2$)$_3$N(CH$_3$)$_2$$^+$CH$_2$COO$^-$ | Oleamidopropyl betaine | Mackam HV (McIntyre) Incronam OP30 (Croda) |
| (CO)NH(CH$_2$)$_3$N(CH$_3$)$_2$CH$_2$CH(OH)CH$_2$R R = hydrolyzed collagen moiety | Oleamidopropyldimonium hydroxypropyl hydrolyzed collagen | Mackpro OLP (McIntyre) |
| (CO)NH(CH$_2$)$_3$N(CH$_3$)$_2$$^+$CH$_2$CH(OH)CH$_2$SO$_3$$^-$ | Oleamidopropyl hydroxysultaine | |
| (CO)NH(CH$_2$)$_3$N(CH$_3$)$_2$$^+$CHCH(OH)CH$_2$OH* Cl$^-$ | Oleamidopropyl PG-dimonium chloride | Lexquat AMG-O (Inolex) |
| (CO)NCH$_3$CH$_2$COOH | Oleoyl sarcosine | Crodasinic O (Croda) Hamposyl O (Hampshire) |
| (CO)NH(CH$_2$)$_2$N(CH$_2$CH$_2$OH)CH$_2$CH(OH)CH$_2$SO$_3$$^-$Na$^+$ | Sodium oleoamphohydroxypropyl sulfonate | Miranol OS-D (Rhodia) |
| (CO)(OCH$_2$CH$_2$)nO(CO)— n is average of polydisperse compositions | PEG-# Dioleate Where # is 4 thru 150 and correspond to n | Kessco PEG 400 Dioleate (Stepan) Kessco PEG 4000 Dioleate (Stepan) |

TABLE 1-continued

| Oleyl-Based-X Groups | | |
|---|---|---|
| Substructure-X | INCI Name | Example Trade Names |
| (CO)NH(CH2CH2O)nH<br>n is average of polydisperse compositions | PEG-7 Oleamide | Kessco PEG 6000 Dioleate (Stepan)<br>Ethomid O/17 (Akzo) |
| N(CH$_2$CH$_2$O)xH<br>\|<br>(CH$_2$CH$_2$O)yH | PEG-# Oleamine<br>Where # is 2 thru 30 and corresponds to x + y | Ethomeen O/12 (Akzo)<br>Ethomeen O/15 |
| (CO)(OCH$_2$CH$_2$)nOH<br>n is average of polydisperse compositions | PEG-# Oleate<br>Where # is 2 through 150 and correspond to n | Kessco Diglycol Oleate (Stepan)<br>Ethofat O/15 (Akzo)<br>Kessco PEG 600 Monooleate (Stepan) |
| NCH$_3$(CH$_2$CH$_2$O)xH$^+$ * Cl-<br>\|<br>(CH$_2$CH$_2$O)yH | PEG-# Oleammonium chloride<br>Where # is 3 through 15 and correspond to x + y | Ethoquad O/12H (Akzo)<br>Ethoquad O/25 |
| (CO)NHCH$_2$CH$_2$N(CH$_2$CH$_2$OH)(CH$_2$COONa)<br>(CO)NHCH$_2$CH$_2$N(CH$_2$CH$_2$OH)(CH$_2$CH$_2$COONa) | Sodium Oleoamphoacetate<br>Sodium Oleoamphopropionate | Miranol OM (Rhodia)<br>Miranol OM-SF (Rhodia) |
| (CO)OCH$_2$CH$_2$SO$_3$Na<br>OSO3Na | Sodium Oleoyl isethionate<br>Sodium Oleyl Sulfate | |
| (CO)NHCH$_2$CH$_2$OCOCH(SO$_3$Na)CH$_2$COONa | Disodium oleamido MEA sulfosuccinate | Mackanate OM (McIntyre)<br>Reowpol SB E 280 (Rewo) |
| NHCH$_2$CH(CH$_3$)OCOCH(SO$_3$Na)CH$_2$COONa | Disodium oleamido MIPA sulfosuccinate | Makanate OP (McIntyre)<br>Emcol 4161L (Witco) |
| NH(CH$_2$CH$_2$O)nCOCH(SO$_3$Na)CH$_2$COONa | Disodium Oleamido PEG-2 Sulfosuccinate<br>(also diammonium oleamido PEG-2 sulfosuccinate) | Mackanate OD-35 (McIntyre)<br>Geropon SBG-280 (Rhodia) |
| (CO)OCH$_2$CH(OH)CH$_2$OH | Glyceryl Oleate | Aldol MO (Lonza)<br>Witconol 2421 (Witco) |
| 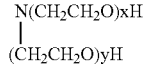 | Sorbitan Oleate | Crill 4 (Croda)<br>Witconol 2500 (Witco) |
| PEG derivatized<br>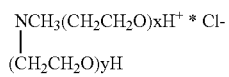 | PEG-# sorbitan oleate<br>PEG-# sorbitan tetraoleate<br>PEG-# sorbitan hexacleate<br>Where # varies from 2 to 50 and corresponds to the level of polyethylene glycol derivatization | Nikko TO 106 (Nikko)<br>Rheodol 460 (Kao)<br>Atlas G-1096 (ICI) |
| N$^+$(CH$_2$CH$_2$OH)$_2$CH$_2$CO$_2^-$ | Dihydroxyethyl oleyl glycinate | |
| OCH$_2$CH(OH)CH$_2$(OCH$_2$CH$_2$)nOH | PEG-# Glyceryl Oleate<br>Where # ranges from 10-30 and corresponds to the average n | Nikkol TMGO-15 (Nikko)<br>Tagat O (Goldschmidt) |
| Ester of polyglyceryl-X and oleic acid | Polyglyceryl-# oleate<br>Where # is the average repeating units of a glycerin polymer | Abil WS 08 (Goldschmidt)<br>Emulsunt 1055 (ISP)<br>Nikkol Decaglyn 1-O (Nikko) |
| —(OCH2CH2)nOH<br>n is average of polydisperse compositions | Oleth-# where # is 3, 4, 5, 6, 7, 8, 9, 10, 12, 15, 16, 20, 23, 25, 30, 40, 44, 50 and corresponds to n | Volpo 10 (Croda)<br>Marlowet OA-5 (Huls)<br>Volpo 20 (Croda) |
| —(OCH2CH2)nOCH2COOH<br>n is average of polydisperse compositions | Oleth-# Carboxylic Acid<br>Where # is 3, 6, 10 and corresponds to n | Akypo RO-20 (Chem Y)<br>Akypo RO-50 (Chem Y) |
| —(OCH2CH2)nOPO2OH<br>n is average of polydisperse compositions | Oleth-# Phosphate<br>Where # is 3, 4, 5, 10, 20 and corresponds to n | Crodafos N-3 (Croda)<br>Crodafos N-10 (Croda) |

TABLE 1-continued

Oleyl-Based-X Groups

| Substructure-X | INCI Name | Example Trade Names |
|---|---|---|
| —COCH(SO3Na)CH2COONa | Disodium oleyl sulfosuccinate | |
| —(OCH2CH2)nO—COCH(SO3Na)CH2CO2Na | Disodium Oleth-3 Sulfosuccinate | Incrosul OTS (Croda) |
| —(OCH2CH2)nOSO3⁻1/2 Mg²⁺ | Magnesium Oleth sulfate n = 1-4 on average | Mixture in Texapon ASV (Henkel) |

Some non-limiting examples of ricinoleyl-based olefin compounds include those having the following structure:

$$CH_3(CH_2)_5CH(OH)CH_2CH=CH(CH_2)_7-X$$

Examples of substructures that may be used as the —X group are provided in Table 2.

TABLE 2

Ricinoleyl-Based —X Groups

| Substructure —X | INCI Name | Example Trade Names |
|---|---|---|
| (CO)N(CH₂CH₂OH)₂ | Ricinoleamide DEA | Mackamide R (McIntyre) |
| (CO)NH(CH₂)₃N(CH₃)₂⁺CH₂COO⁻ | Oleamidopropyl betaine | Rewoteric AM R 40 (Rewo Chemische) |
| | | Mackam RA (McIntyre) |
| (CO)NH(CH₂)₃N(CH₃)₃⁺CH₃OSO₃⁻ | Ricinamidopropyltrimonium methosulfate | Rewoquat RTM 50 (Rewo) |
| (CO)NH(CH₂CH₂O)nH n is average of polydisperse compositions | PEG-40 Ricinoleamide | |
| (CO)O(CH₂CH₂O)nH n is average of polydisperse compositions | PEG-# Ricinoleate Where # is 2 through 9 and correspond to n | Atlas G4929 (ICI) |
| (CO)NHCH₂CH₂OCOCH(SO₃Na)CH₂COONa | Disodium ricinoleamido MEA sulfosuccinate | Mackanate RM (McIntyre) Monamate RMEA-40 (Mona) |
| (CO)OCH2CH(OH)CH2OH | Glyceryl ricinoleate | Aldo MR (Lonza) Tegin RZ (Goldschmidt) |
| (CO)OCH2CH(OH)CH2(OCH2CH2)nOH | PEG-# Glyceryl Ricinoleate | |

Some non-limiting examples of undecylenyl-based olefin compounds include those having the following structure:

$$CH_2=CH(CH_2)_8-X$$

Examples of substructures that may be used as the —X group are provided in Table 3.

TABLE 3

Undecylenyl-Based —X Groups

| Substructure —X | INCI Name | Example Trade Names |
|---|---|---|
| (CO)N(CH₂CH₂OH)₂ | Undecylenamide DEA | Rewocid DU 185 (Rewo Chemische) |
| (CO)NH(CH₂)₃N(CH₃)₂→0 | Undecylenamidopropylamine oxide | |
| (CO)N(CH₃)₂⁺CH₂COO⁻ | Undecylenamidopropyl betaine | |
| (CO)NHCH₂CH₂OCOCH(SO₃Na)CH₂COONa | Disodium undecylenamido MEA sulfosuccinate | Emcol 5330 (Witco) Rewocid SB U 185 (Rewo) |

In addition to the above-described olefin compounds, the following olefin compounds are examples of olefin compounds that may be used in the present invention:

1. Disodium Dihydroxyethyl Sulfosuccinylundecylenate (commercially available as Grillosan DS 7911 from RITA).

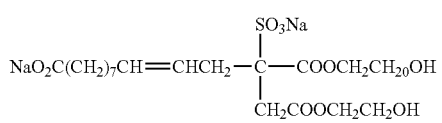

2. Disodium PEG-8 Ricinosuccinate (commercially available as Grillosan 8C12 from RITA).

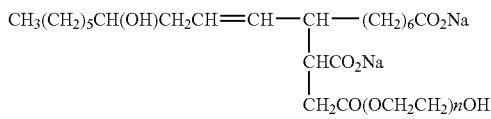

3. Sodium Bisglycol Ricinosulfosuccinate (commercially available as Grillosol 8C from RITA).

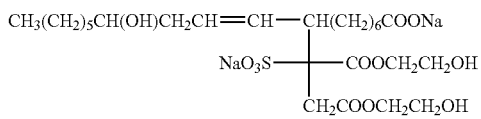

In some preferred embodiments, the olefin compound is water soluble or water dispersible. In some preferred embodiments, the olefin compound has an HLB equal to or greater than 8. Preferred olefin compounds have the hydrophilic group connected to the olefin group via an amide, ether, quaternary ammonium, or amine group. Most preferably, the olefin compound is an oleyl-, ricinoleyl-, or undecylenyl-based derivative where the hydrophilic group is connected to the olefin group via an amide, ether, quaternary ammonium group, or amine group.

Some examples of preferred olefin compounds include sodium oleoyl N-methyl taurate, oleth-X where X is 3-20, oleth-X phosphate where X is 3-20, oleth-X carboxylate where X is 3-20, oleth sulfate, oleamidopropyl betaine, ricinoleamidopropyl betaine, and oleylmethylbis(hydroxyethyl) ammonium chloride.

The olefin compound is preferably an oleyl-based compound, and in particular sodium N-methyl oleoyl taurate commercially available as Geropon T-77 from Rhodia; oleamidopropylbetaine commercially available as Mackam HV from McIntyre; Oleth-10 and 20 commercially available as Volpo-10 and Volpo-20 from Croda; Oleth-10 phosphate commercially available as Crodofos-10 from Croda; and oleylmethylbis(hydroxyethyl)ammonium chloride commercially available as Ethoquad O/12 PG from Akzo Nobel.

The olefin compound is present in the first part, the second part, or both the first and second parts in an amount such that when the first part and second part are combined, it is present within the disinfecting composition at a concentration ranging from about 0.005% to about 50% by weight, generally from about 0.05% to about 10% by weight, and from about 0.1% to about 5% by weight. Mixtures of olefin compounds are also encompassed within this invention. For example, one type of olefin compound may be present in the first part, with a different type present in the second part.

Various optional ingredients may also be present in the first part, the second part, or both first and second parts of the two-part system. Such ingredients include (but are not limited to) wetting agents, builders, textural modifiers, film-forming polymers, surfactants, colorants and mixtures thereof. The wetting agents facilitate contact of the disinfecting composition with the skin or surface, and can be selected from those materials recognized to provide this effect, in both identity and amount. Builders help boost the cleaning performance of surfactant systems and are typically associated with materials that are capable of complexing with polyvalent cations, such as calcium and magnesium. Textural modifiers are those materials which primarily affect the body of the mixed disinfecting composition in terms of retention, flow and lubricity. These include thickening agents such as alkyl celluloses, alkoxy celluloses, xanthan gum, guar gum, and polyacrylamide derivatives, of which the polymer of 2-acrylamido-2-methylpropane sulfonic acid is a preferred example. Inorganic thickening agents include hectorite, synthetic hectorite, magnesium aluminum silicate, bentonite, montmorillonite, and amorphous silicon dioxide. Thickening can also be achieved by the combination of selective surfactant classes. Other textural modifiers include lanolin derivatives, acyl lactylates, polyethylene glycol, glyceryl esters, and mixtures thereof. Skin conditioning and skin healing agents include glycerin, sorbitol, pyrrolidone carboxylic acid, mineral oils, silicone oils, protein hydrolysates, petrolatum, hydrocarbon emollient alcohols and esters, allantoin, aloe vera extracts, and urea. Film-forming polymers include the above-referenced polyacrylamides, as well as the class of poly(vinyl alcohols/vinyl acetates), polyurethanes, chitosan, polyvinyl pyrrolidone, and polyvinyl pyrrolidone copolymers.

In a further embodiment, a method for disinfecting a substrate is disclosed, wherein the method comprises contacting the substrate with an effective amount of the disinfecting composition formed by combining the first part and the second part of the two-part disinfecting system of this invention. In this context, the substrate may be any surface or material in need of, or that would benefit from, such disinfection, including (but not limited to) skin or tissue, as well as body fluids and mucosal membranes. For example, the substrate may be a wound where disinfection would aid healing. The substrate may be the inside of an animal's mouth where disinfection would help prevent gingivitis and halitosis. The substrate may include any item that is intimately placed in, on, or around the body of an animal, such as dentures, braces, and contact lenses. In a specific application, the substrate is the teat of a dairy cow, goat or sheep. In addition, the substrate may be any surface of a food product, such as meat, fish, fruits and vegetables. The substrate may also include food contact surfaces, and nonfood contact surfaces in food processing plants. The substrate may include any hard surface, such as (but not limited to) floors, walls, countertops, containers, instruments and/or equipment found in homes, hospitals, and manufacturing facilities. In a specific application, the hard surfaces may include housing and equipment surfaces in animal rearing and production environments. Materials that may benefit from disinfection include, for example, process waters, such as flume waters, cooling tower waters, livestock drinking waters, equipment, and facility cleaning solutions.

In a further aspect of this invention, this invention is directed to a method for making a disinfecting composition comprising combining the first part and the second part of the two-part disinfecting system. In one embodiment, the first and second parts are both aqueous solutions, emulsions, microemulsions, creams or gels, and may be adapted to be combined in equal or different volumes. In another embodiment, at least one of the first or second parts is in a concentrated, non-aqueous or solid form, and the concentrated, non-aqueous or solid form is first diluted with or dissolved in water, and then combined with the other part. Alternatively, the dilution or dissolving step can occur prior to combination with the other part, or simultaneous with combination.

The following examples are provided for the purpose of illustration, not limitation.

EXAMPLES

Example 1

A series of two-part acidified chlorite products were prepared by combining an acid part comprising 2.64% lactic acid, 10.00% glycerin, 0.30% FD&C Yellow #5, 0.30% xanthan gum, 0.04% sodium benzoate and an olefin compound formulated at 0.045M (or no olefin compound for the control) with a chlorite part containing 0.64% sodium chlorite and sufficient quantities of sodium hydroxide to yield a pH of 2.75 when mixed 1:1. The rate of color fading at 35° C. was quantified by UV/Vis spectroscopy at 425 nm.

TABLE 4

Olefin Compounds and Effect on Color Fading at 35° C.

| | | Time After Mixing (** >50% of Initial Color Intensity Remaining) | | | | |
|---|---|---|---|---|---|---|
| Olefin Compound (0.045M) | Weight Percent* | ½ hour | 1 hour | 2 hour | 3 hour | 4 hour |
| Sodium N-methyl oleoyl taurate | 1.91 | ** | ** | ** | ** | ** |
| Oleth-10 | 3.19 | ** | ** | ** | ** | ** |
| Oleth-10 phosphate | 3.55 | ** | ** | ** | ** | ** |
| Oleamidopropyl betaine | 1.91 | ** | ** | ** | ** | ** |
| Oleylmethylbis (hydroxyethyl) ammonium chloride | 1.81 | ** | ** | ** | ** | ** |
| Disodium oleamido MEA sulfosuccinate | 2.48 | ** | ** | ** | ** | ** |
| Control (no olefin) | — | ** | — | — | — | — |

*The weight percent corresponds to the active weight percent of olefin derivative in the acid part. This corresponds to an equal molar comparison of the olefin derivative at 0.0225M in the mixed product composition.

The olefin compounds in Table 4 significantly extended the color marking longevity vs the control.

Example 2

Three compositions were prepared according to example 1 where the olefin compound was 0.4% sodium oleoyl N-methyl taurate (Geropon T-77), or a saturated homolog of 0.4% sodium cocoyl N-methyl taurate (Geropon TC 270), or a no olefin control. All products possessed a mixed product pH of 2.75. The rate of color fading at 35° C. was quantified by UV/Vis spectroscopy at 425 nm.

TABLE 5

Comparison of a Olefin vs Non-Olefin Compound and the Effect of Color Fading at 35° C.

| | Time After Mixing (** >50% of Initial Color Intensity Remaining) | | | | |
|---|---|---|---|---|---|
| Component | ½ hour | 1 hour | 2 hour | 3 hour | 4 hour |
| Sodium N-methyl oleoyl taurate | ** | ** | ** | ** | — |
| Sodium N-methyl cocoyl taurate | ** | — | — | — | — |
| Control (no olefin) | ** | — | — | — | — |

Table 5 illustrates that the olefin compound (sodium N-methyl oleoyl taurate) extended the colorant intensity longer while the saturated cocoyl homolog did not.

Example 3

A series of two-part acidified chlorite products were prepared that when combined 1:1 produced compositions containing 1.32% lactic acid, 0.32% sodium chlorite, an olefin compound formulated at a 0.0225M, and sufficient quantities of sodium hydroxide to produce a mixed product pH of 2.75. The rate of chlorine dioxide generation was determined by UV/Vis spectroscopy at 360 nm (54.31 ppm/A.U. cm).

TABLE 6

Olefin Compounds and the Rate of Chlorine Dioxide Generation

| | | Time After Mixing (ppm Chlorine Dioxide) | | | | |
|---|---|---|---|---|---|---|
| Olefin Compound | Weight Percent* | 1 hour | 2 hour | 3 hour | 4 hour | 5 hour |
| Sodium N-methyl oleoyl taurate | 1.91 | 4 | 5 | 5 | 6 | 7 |
| Oleth-10 | 3.19 | 10 | 16 | 21 | 25 | 28 |
| Oleth-10 phosphate | 3.55 | 7 | 14 | 17 | 21 | 25 |
| Control (no olefin) | — | 40 | 62 | 83 | 96 | 110 |

*Weight percents correspond to the active weight percent of the olefin derivative in the acid part. This corresponds to an equal molar comparison of the olefin derivative at 0.0225M in the mixed product composition.

Table 6 illustrates that the olefin compounds significantly slowed the rate of chlorine dioxide generation relative to the control.

Example 4

Three acidified chlorite compositions were prepared according to Example 1 where the olefin compound was 1.4% sodium oleoyl taurate (Geropon T-77), or 1.4% alpha olefin sulfonate (Bioterge AS-40, Stepan), or a no olefin control, with a chlorite part containing 0.64% sodium chlorite and sufficient quantities of sodium hydroxide to achieve a pH of 2.75 when mixed 1:1. The rate of sodium chlorite consumption was quantified using a standard iodometric titration method.

TABLE 7

Olefin Compounds and the Rate of Sodium Chlorite Consumption

| | Time After Mixing (** >50% Initial NaClO2 Level) | | | | |
|---|---|---|---|---|---|
| Olefin Compound | 1 hour | 2 hour | 3 hour | 4 hour | 5 hour |
| Sodium N-methyl oleoyl taurate | ** | ** | ** | ** | ** |
| Alpha olefin sulfonate | ** | ** | ** | — | — |
| Control (no olefin) | ** | — | — | — | — |

Results in Table 7 illustrate that olefin compounds significantly slowed the rate of sodium chlorite consumption. Sodium N-methyl oleoyl taurate (Geropon T-77) exhibited a stronger effect than alpha olefin sulfonate (Bioterge AS-40) on an equal weight-base comparison.

Example 5

The germicidal performance of a two-part acidified chlorite composition was evaluated using the AOAC Germicidal and Detergent Sanitizing Action test method with a 15 second exposure period. A disinfectant composition was prepared according to Example 1 with 0.4% sodium oleoyl N-methyl taurate as the olefin compound. Ninety-nine mL samples were taken initially, at 2.5 hours, and at 5 hours after mixing and inoculated with 1 mL of the bacterial challenge. Samples from the resulting solutions were neutralized, plated, and enumerated using standard methods. In parallel, a water control was tested in place of the disinfectant composition.

TABLE 8

Germicidal Testing of Acidified Chlorite Composition
(15 sec. Exposure Time)

| Bacteria | Time After Mixing (** no surviving bacteria observed) | | | Control Bacterial Count (Log CFU/mL) |
|---|---|---|---|---|
| | Initial | 2.5 hours | 5 hours | |
| *Pseudomonas aeruginosa* ATCC 15442 | ** | ** | ** | 6.92 |
| *Escherichia coli* ATCC 11229 | ** | ** | ** | 6.97 |
| *Klebsiella pneumoniae* ATCC 4352 | ** | ** | ** | 6.81 |
| *Enterobacter aerogenes* ATCC 13048 | ** | ** | ** | 7.20 |
| *Streptococcus uberis* ATCC 27958 | ** | ** | ** | 6.51 |
| *Streptococcus dysgalactiae* ATCC 27957 | ** | ** | ** | 5.93 |

The results in Table 8 show that the present invention is effective at killing a variety of microorganisms compared to a control having a bacterial count of almost at least six logs in every example.

Example 6

TABLE 9

A two part teat disinfectant product to mixed 36.57:1 by volume Acid Part + Chlorite Part.

| | wt % |
|---|---|
| Acid Part | |
| Lactic Acid | 2.95% |
| Propylene Glycol | 10.00% |
| Lanolin Ethoxylate | 1.00% |
| FD&C Blue #1 | 0.05% |
| FD&C Yellow #5 | 0.10% |
| Linear Dodecylbenzene Sulfonic Acid | 2.00% |
| Mackam HV[1] | 2.00% |
| Xanthan Gum | 0.30% |
| Sodium Benzoate | 0.18% |
| Potassium Hydroxide | 0.18% |
| DI Water | q.s. |
| Chlorite Part | |
| Sodium Chlorite, 25% | 15.00% |
| DI Water | q.s. |

[1]Mackam HV: Oleamidopropyl Betaine (McIntyre)

Example 7

TABLE 10

Two-part teat disinfectant product to be mixed 1:1 by volume

| | wt % |
|---|---|
| Acid Part | |
| Mandelic Acid | 3.00% |
| Glycerin | 5.00% |
| FD&C Yellow #5 | 0.30% |
| Hydroxyethyl Cellulose | 1.00% |
| Sodium Benzoate | 0.20% |
| Bioterge AS-40[2] | 0.50% |

TABLE 10-continued

Two-part teat disinfectant product to be mixed 1:1 by volume

| | wt % |
|---|---|
| Crodafos 10[3] | 0.50% |
| DI Water | q.s |
| Chlorite Part | |
| Sodium Chlorite | 0.64% |
| Polysulfonic Acid[4] | 15.00% |
| Edetate Disodium | 0.17% |
| Sodium Hydroxide | 0.56% |
| DI Water | q.s. |

[2]Bioterge AS-40: C14-16 Olefin Sulfonate (Stepan)
[3]Crodafos 10: Oleth-10 Phosphate (Croda)
[4]Polysulfonic Acid: Cosmedia HSP (Cognis)

Example 8

TABLE 11

Two-part teat disinfectant product to be mixed 1:1 by volume

| | wt % |
|---|---|
| Acid Part | |
| Lactic Acid | 2.64% |
| Glycerin | 10.00% |
| FD&C Yellow #5 | 0.30% |
| Xanthan Gum | 0.30% |
| Sodium Benzoate | 0.04% |
| Volpo-10[5] | 2.00% |
| Octanoic Acid | 0.20% |
| DI Water | q.s. |
| Chlorite Part | |
| Sodium Chlorite | 0.64% |
| Edetate Disodium | 0.04% |
| Sodium Hydroxide | 0.032% |
| DI Water | q.s. |

[5]Volpo-10, Oleth-10 (Croda)

Example 9

TABLE 12

A two part hard surface cleaner/sanitizer to be mixed 1:1 by volume.

| | wt % |
|---|---|
| Acid Part | |
| Citric Acid | 2.00% |
| Neodol 1-5[6] | 1.50% |
| Volpo 10 | 1.00% |
| Dowanol DnB[7] | 3.00% |
| DI Water | q.s. |
| Chlorite Part | |
| Sodium Chlorite, 25% | 2.00% |
| DI Water | q.s. |

[6]Neodol 1-5: C11 Akyl Ethoxylate EO = 5 (Shell)
[7]Dowanol DnB: Propylene Glycol n-Butyl Ether (Dow)

Example 10

TABLE 13

A two part mouth rinse to be mixed 1:1 by volume:

| | wt % |
|---|---|
| Acid Part | |
| Malic Acid | 2.70% |
| Propylene Glycol | 20.0% |
| Menthol | 0.07% |
| Sodium Benzoate | 0.05% |
| Sodium Saccharin | 0.50% |
| FD&C Blue #1 | 1.5 ppm |
| Sodium Oleth Sulfate | 0.10% |
| DI Water | q.s. |
| Chlorite Part | |
| Sodium Chlorite | 0.27% |
| Sodium Fluoride | 0.10% |
| Sodium Hydroxide | 0.07% |
| DI Water | q.s. |

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A two-part disinfecting system comprising a first part and a second part adapted to be mixed to yield an aqueous disinfecting composition, wherein the first part comprises a chlorite and the second part comprises an acid, and wherein the first part contains an olefin compound having the formula:

$$CH_3(CH_2)_7CH\!=\!CH(CH_2)_7(CO)NCH_3CH_2CH_2SO_3Na$$

wherein the olefin compound is present in the first part so that, when the first part and second part are combined, the olefin compound is present within the disinfecting composition at a concentration ranging from about 0.005% to about 50% by weight, and wherein the acid is present in the second part in an amount so that, when combined with the first part, the pH of the disinfecting composition is between about 2 and about 5.

2. The system of claim 1, further comprising an oxidizable colorant present in the first part, the second part, or both the first part and second part.

3. The system of claim 1, wherein the olefin compound is present in the second part in an amount so that, when the first part and second part are combined, it is present within the disinfecting composition at a concentration ranging from 0.05% to 10% by weight.

4. The system of claim 1, wherein the chlorite is a metal chlorite.

5. The system of claim 4, wherein the metal chlorite is an alkali or alkaline earth metal chlorite.

6. The system of claim 5, wherein the metal chlorite is sodium chlorite or potassium chlorite.

7. The system of claim 1, wherein the chlorite is present in the first part in an amount so that, when combined with the second part, it is present within the disinfecting composition at a concentration ranging from about 0.005% to about 3% by weight.

8. The system of claim 1, wherein the acid is lactic acid.

9. The system of claim 1, wherein the acid is present in the second part in an amount so that, when combined with the first part, it is present within the disinfecting composition at a concentration ranging from about 0.05% to about 10% by weight.

10. The system of claim 2, wherein the oxidizable colorant is a food, drug and cosmetic colorant.

11. The system of claim 1, wherein the acid has a $pK_a$ ranging from 2 to 5.

12. The system of claim 1, wherein the acid is an organic acid, an inorganic acid, and mixtures thereof.

13. The system of claim 1, wherein the organic acid is glycolic acid, lactic acid, malic acid, mandelic acid, citric acid, tartaric acid, adipic acid, succinic acid, malonic acid, heptanoic acid, octanoic acid, nonanoic acid, benzoic acid, gluconic acid, or a mixture thereof.

14. The system of claim 1, wherein the inorganic acid is sulfuric acid, sulfamic acid, phosphoric acid, hydrochloric acid, nitric acid, or a mixture thereof.

15. The system of claim 1, wherein both the first part and the second part are independently in the form of an aqueous solution, emulsion, microemulsion, cream or gel.

16. The system of claim 1, wherein the first part, the second part, or both the first and second parts further comprise a textural modifier, wetting agent, thickening agent, skin conditioner, healing agent, film-forming polymer, surfactant, preservative, or a mixture thereof.

* * * * *